United States Patent [19]
Korenfeld

[11] Patent Number: 5,941,873
[45] Date of Patent: Aug. 24, 1999

[54] SURGICAL LASER SMOKE PLUME EVACUATOR

[76] Inventor: Michael S. Korenfeld, 16681 Clayton Rd., St. Louis, Mo. 63011

[21] Appl. No.: 08/685,918

[22] Filed: Jul. 22, 1996

[51] Int. Cl.$^6$ .................................................. A61B 17/00
[52] U.S. Cl. .................................. 606/1; 604/313; 606/4
[58] Field of Search ............................... 606/1, 4, 5, 161, 606/166; 604/313; 600/235, 236

[56] References Cited

U.S. PATENT DOCUMENTS

| | | |
|---|---|---|
| 3,074,407 | 1/1963 | Moon et al. . |
| 4,053,984 | 10/1977 | Moss . |
| 4,884,559 | 12/1989 | Collins . |
| 4,921,492 | 5/1990 | Shultz et al. . |
| 5,015,243 | 5/1991 | Schifano . |
| 5,054,906 | 10/1991 | Lyons . |
| 5,070,860 | 12/1991 | Grounauer . |
| 5,108,412 | 4/1992 | Krumeich et al. . |
| 5,156,618 | 10/1992 | Fiore et al. . |
| 5,171,254 | 12/1992 | Sher . |
| 5,341,798 | 8/1994 | Grounauer . |
| 5,433,190 | 7/1995 | Sunalp . |
| 5,441,040 | 8/1995 | Williams, Jr. ............................ 600/236 |
| 5,499,964 | 3/1996 | Beck et al. . |

OTHER PUBLICATIONS

Pfizer, Valleylab, Inc., Accuvac Smoke Evacuation Attachment 1995 brochure.

Medtek Devices, Inc., Bulletins #96–2 and 95–5 Buffalo Filter Electrosurgical Accessories for Plume safe systems.

Storz® *Ophthalmic Instruments* catalogue, 1988, p. 248, McBratney Aspirating Speculum, No. E4117, and p. 246, Simcoe eye Speculum, No. E4108 S.

Garden, J.M., et al., Papillomavirus in the vapor of carbon dioxide laser–treated verrucae, JAMA, 1988; 259: 1199–1202.

Sawchuk, W.S., et al., Infectious papillomavirus in the vapor of warts treated with carbon dioxide laser or electrocoagulation: Detection and protection, J. AM. Acad. Dermatol, 1989; 21;41–49.

Mihashi, IS., et al., Some problems about condensates induced by C02 laser irradiation, Fourth International Society for Laser Surgery, Tokyo, Nov. 1981.

Department of Labor, Part II, Occupational Safety and Health Administration, 29 CFR Part 1910.1030, Occupational Exposure to Bloodborne Pathogens: Final Rule, Friday, Dec. 6, 1991.

Puliafito, C.A., et al., High–speed photography of excimer laser ablation of the cornea, Arch. Ophthamol. 1987; 105: 1255–1259.

American National Standard Institute, American National Standard for Safe Use of Lasers in Health Care Facilities, pp. 15 and 16. 1996.

VISX™ Star Examiner Laser Systems brochure, ANSIZI36.3–1996.

*Primary Examiner*—John P. Lacyk
*Assistant Examiner*—Rosiland Kearney
*Attorney, Agent, or Firm*—Blackwell Sanders; Peper Martin; Intellectual Propert Group

[57] ABSTRACT

A surgical laser smoke plume evacuator includes an evacuator body which is formed to a shape which is suitable for placement in normal use position substantially entirely around and adjacent to a tissue site upon which laser surgery is to be performed. The evacuator body has structure for removing smoke therethrough, and a smoke exit portion in communication with and extending from the evacuator body. The smoke exit portion is connectable to vacuum source, to thereby apply a vacuum to the evacuator body and cause smoke which is created at a surgical site during surgery to be removed from the surgical site through the evacuator body and the smoke exit portion.

35 Claims, 6 Drawing Sheets

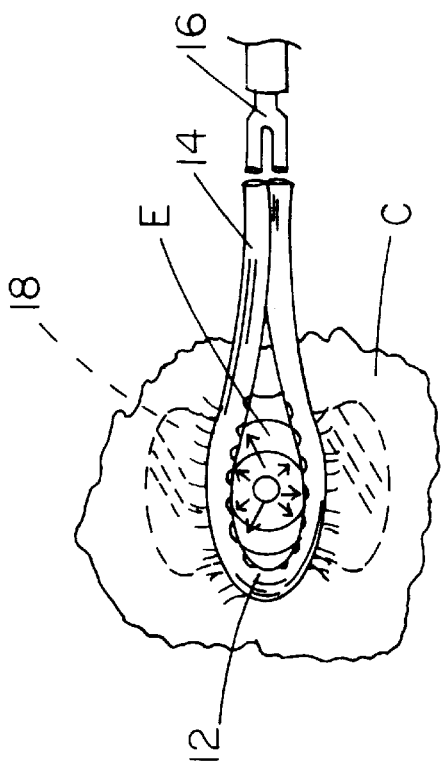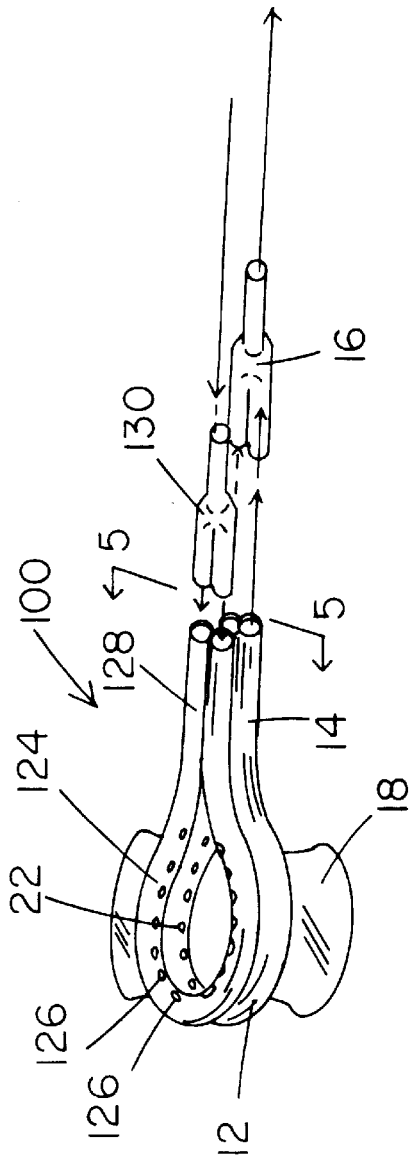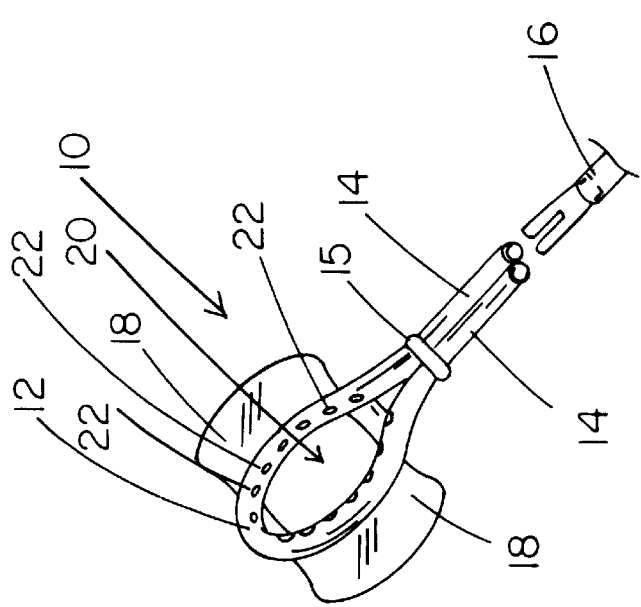
FIG. 1
FIG. 2
FIG. 3

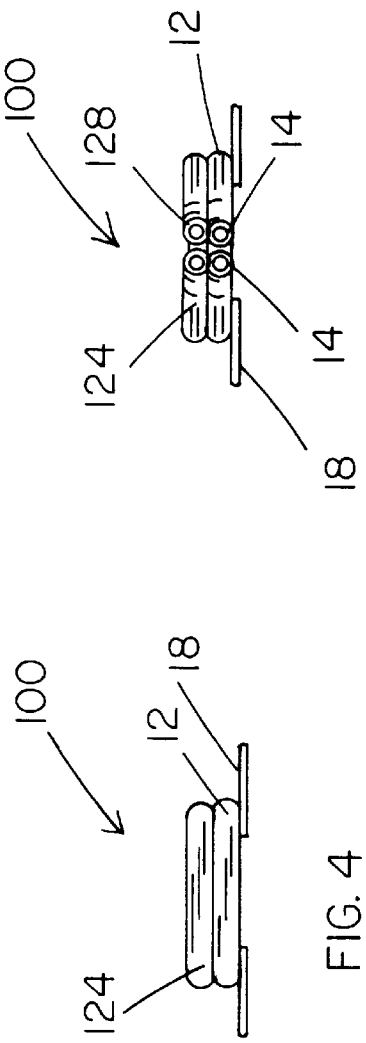
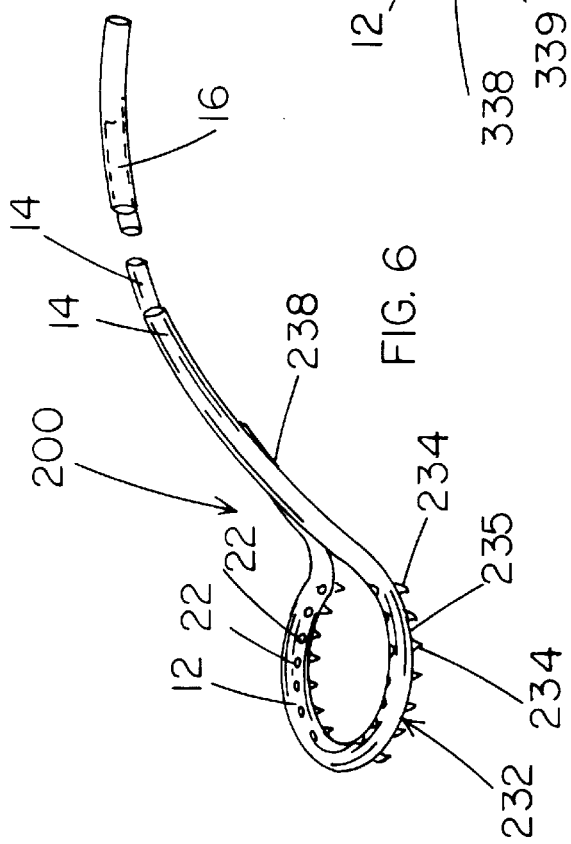

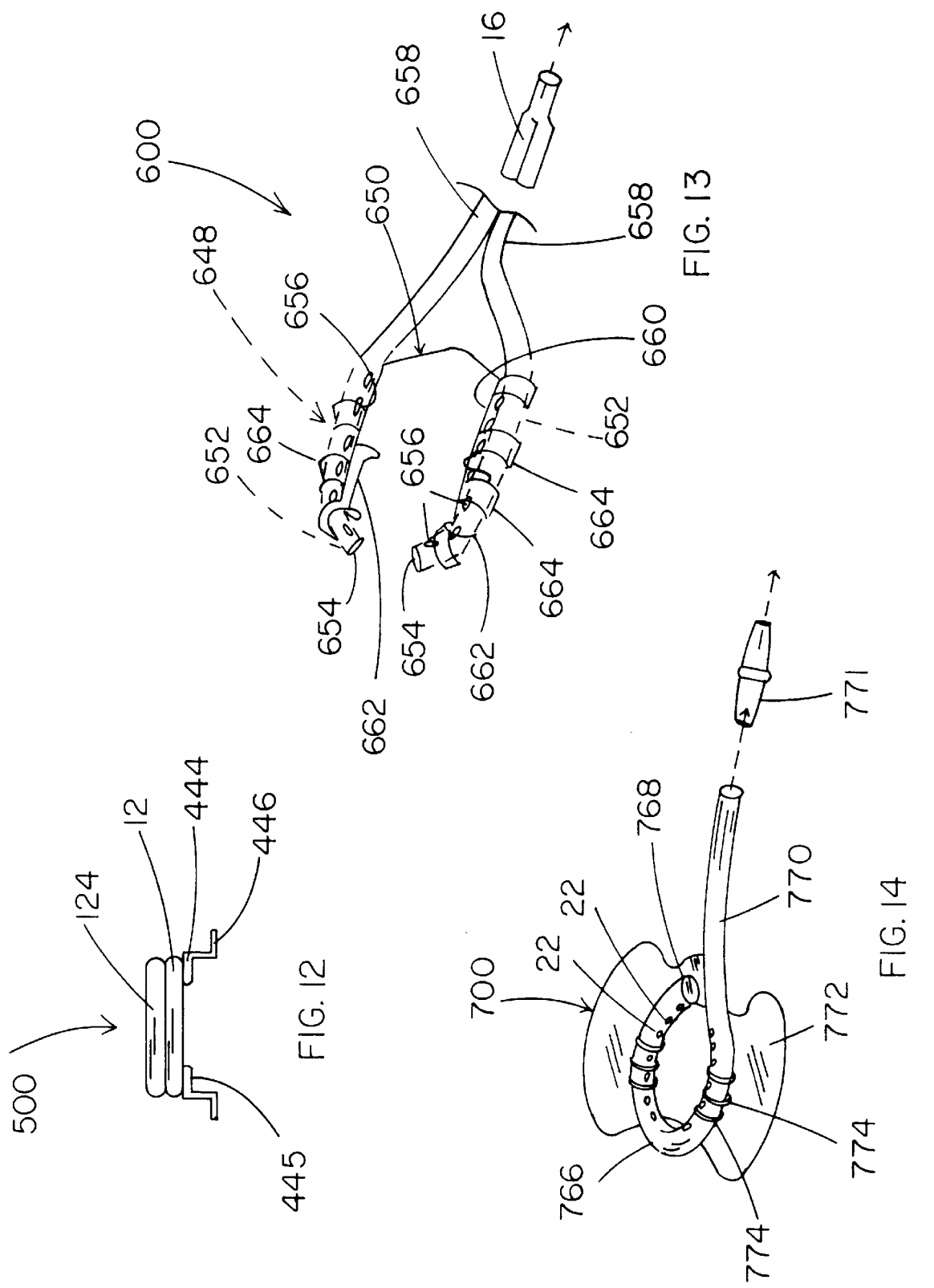

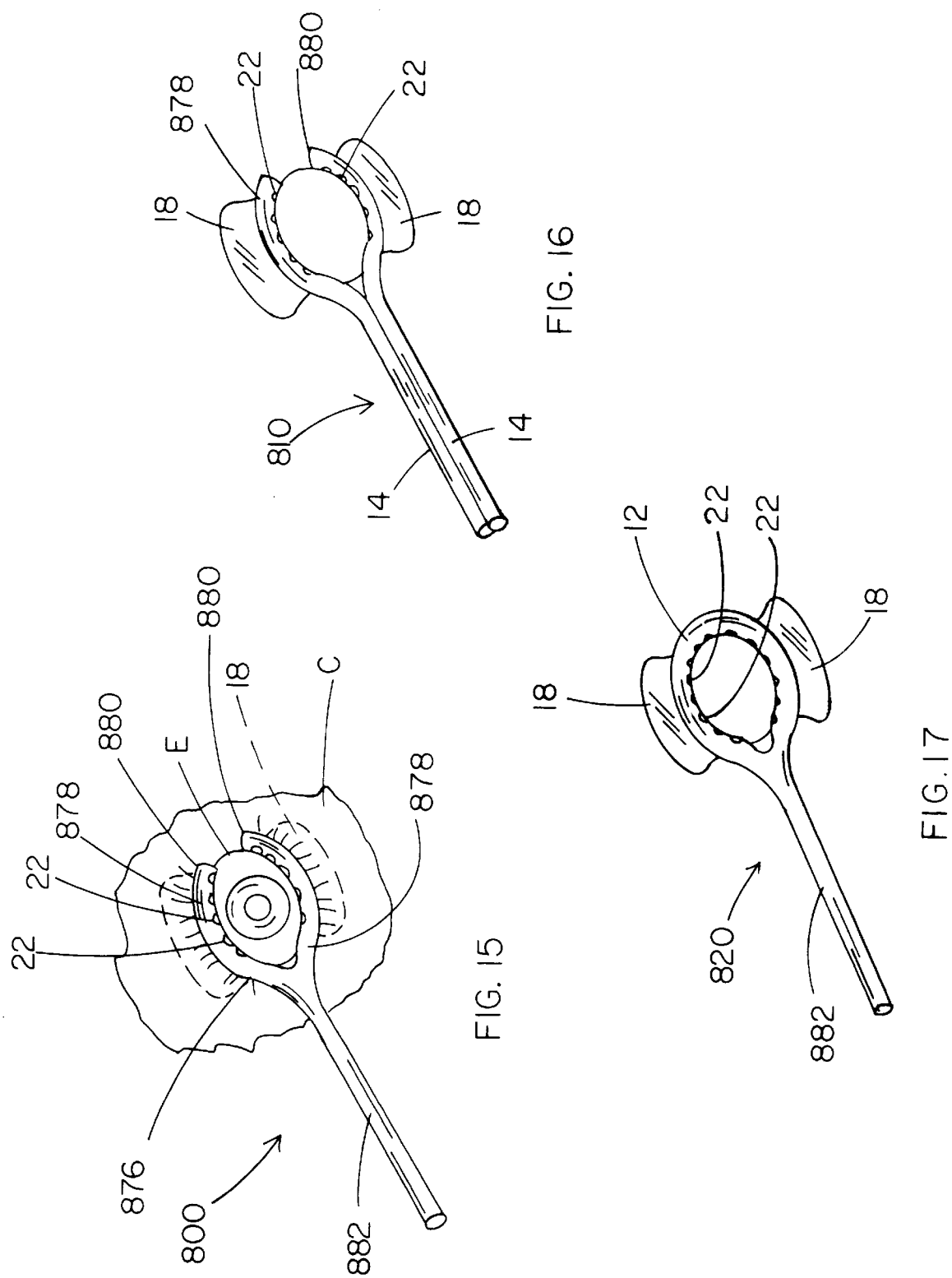

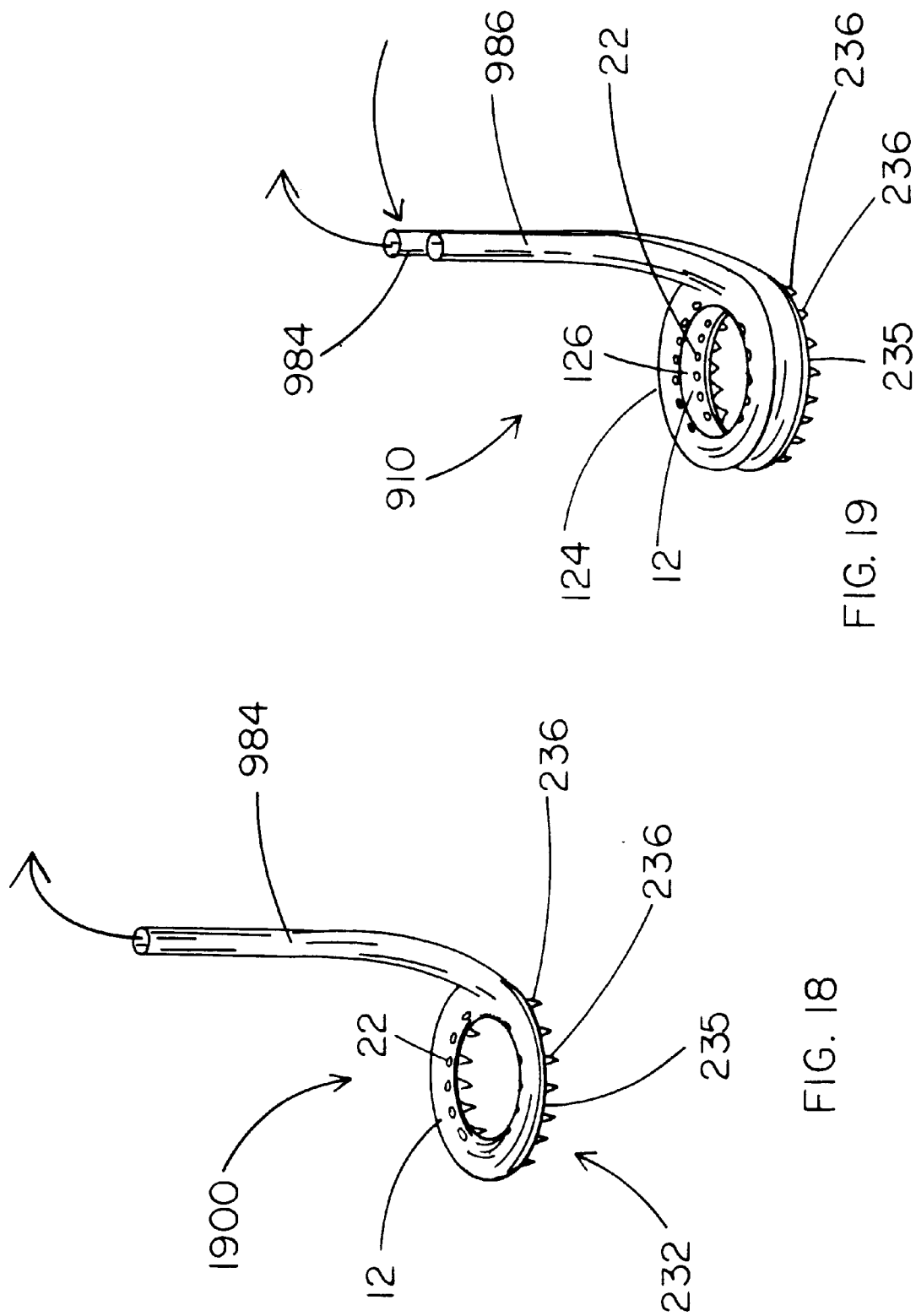

SURGICAL LASER SMOKE PLUME EVACUATOR

FIELD OF THE INVENTION

The present invention relates generally to the removal of the smoke plume generated by a laser during surgical procedures, and more particularly, to a device which is, in some of the disclosed embodiments, an integral speculum and smoke plume evacuator combined, or, in other embodiments, is provided as an independent smoke plume evacuator which can be selectively detachably connected to a speculum for permitting the efficient evacuation of smoke generated from surgical lasers while allowing unperturbed delivery of the laser energy to the surgical site. The new smoke evacuator device can optionally simultaneously afford the capability to vary the fluid mixture that is immediately above the laser-tissue reaction site.

BACKGROUND OF THE INVENTION

There are many different kinds of lasers currently utilized in medical procedures. In some of these techniques the laser-tissue interaction occurs within the body, such as with the Argon laser or YAG laser for intraocular use. When this occurs, no smoke plume is produced. Other types of lasers are focused upon the outside surface of the body such as, for example, the $CO_2$ laser which is used on skin, or the excimer laser, which is used on the surface of the cornea of the eye. When these types of lasers interact with tissue, a plume of smoke is generated which enters the air space above the tissue. This smoke plume has been shown to be composed of water vapor as well as vaporized tissue. A similar smoke plume results from electrical cauterization of body tissues.

Substances contained within the tissue are thrown into the smoke plume as a result of the laser's explosive contact with the target tissue. In the case of $CO_2$ laser smoke, intact papillomavirus (Garden, J. M. et al. *JAMA* 1988,; 259:1199–1202) and intact infectious papillomavirus (Sawchuk, W. S. et at., *J. Am Acad. Dermatol*, 1989; 21:41–49) have been demonstrated when smoke is tested from the interaction of the $CO_2$ laser and virally induced papillomas.

Studies have shown that the smoke generated from $CO_2$ laser treatment of non-infected dog tongue induces a positive Ames' test for microbial mutation (Mihashi, S. et al., paper at Fourth International Society for Laser Surgery, Tokyo, November, 1981). This result indicates some level of carcinogenicity associated with such a laser generated smoke plume, even as a result of surgery on non-infected tissues.

Papillomavirus has been indicated to be a causative agent for some cervical cancers. Thus, the presence of intact papillomavirus in smoke plumes may render laser smoke from this source even more mutagenic.

Investigators such as Garden, J. M. et al. (JAMA 1988,; 259:1199–1202) who have studied the smoke plume from the $CO_2$ laser have recommended efficient evacuation of the smoke that is produced so that the surgeon and other health care workers in the room are not exposed to any potentially infectious or carcinogenic smoke.

The United States Government Department of Labor, Occupational Safety and Health Administration (OSHA) has outlined regulations (Part II, 29 CFR Part 1910.1030, *Occupational Exposure to Bloodborne Pathogens: Final Rule*, Dec. 6, 1991), that require employers to keep work places safe for employees. These guidelines address the goal of avoiding reasonably anticipated occupational exposure of eyes, mouth, other mucous membrane, non-intact skin, or parenteral contact with blood or other potentially infectious materials as a result the performance of an employee's occupational duties.

Potentially infectious materials include any unfixed tissue or organ (other than intact skin) from a human (living or dead) source individual. Under circumstances in which differentiation between bodily fluid types is difficult or impossible, all body fluids are considered potentially infectious materials.

All procedures involving blood or other potentially infectious materials are required under OSHA regulations to be performed in such a manner as to minimize splashing, spraying, spattering, and generation of droplets of these substances. For example, masks in combination with eye protection devises such as goggles or glasses with solid side shields or chin length face shields must be worn whenever splashes, spray, spatter or droplets of blood or other potentially infectious materials may be generated and eye, nose, or mouth contamination can be reasonably anticipated.

Also, vacuum lines must be protected with liquid disinfectant traps and high efficiency particulate air (HEPA) filters or filters of equivalent or superior efficiency are required and must be checked routinely and maintained or replaced as necessary. Finally, OSHA requires that when there is occupational exposure, the employer shall provide, at no cost to the employee, appropriate personal protective equipment such as, but not limited to, gloves, gowns, laboratory coats, face shields or masks and eye protection, and mouthpieces, resuscitation bags, pocket masks, or other ventilation devices. Personal protective equipment must not permit blood or other potentially infectious materials to pass through to or reach the employee's work clothes, street clothes, undergarments, skin, eyes, mouth, or other mucous membranes under normal conditions of use and for the duration of time which the protective equipment will be used.

Surgeons who perform laser operations on the surface of the body routinely encounter the production of smoke commonly referred to as a "plume", from the laser's impact. As the plume of smoke can actually be smelled, it is actually making contact with the mucous membranes of the nose. It is clear that the smoke plume material would be considered potentially infectious by the above-referenced guidelines established by OSHA. Furthermore, since the plume material has been shown to be mutagenic and to transport intact infectious papillomavirus (in the case of $CO_2$ laser, papilloma interactions), an efficient evacuation of this smoke plume, away from the patient, surgeon and other medical personnel is prudent and desirable. The absence of an efficient smoke plume evacuator for surgical lasers which generate a smoke plume appears to be in direct violation of current OSHA regulations.

The American National Standards Institute (ANSI), for Safe Use of Lasers in Health Care Facilities also publishes regulations governing the safe use of surgically induced smoke plumes (ANSI-Z 136.3-1996). In this publication, ANSI defines laser generated Airborne Contaminants (LGAC) in a similar way as OSHA and designates these surgically included smoke plumes as dangerous. These plumes are further stated to be produced by Class 4 lasers, high power Class 3b lasers, and electrosurgical devices and instrumentation. ANSI stipulates that through local exhaust ventilation, the LGAC shall be capture as near as practical to the point of production and either be completely trapped within the system or vented out of the area (see, *American National Standard Fundamentals Governing the Design and Operation of Local Exhaust Systems. ANSI.*

Currently there are two excimer (excited dimer) laser systems approved for use in The United States. Other excimer laser companies also have lasers that are being used in other countries. The Summit Technology, Inc. laser system sold in the United States has no provision for smoke plume evacuation at all. The VISX™ excimer laser system does have a unidirectional smoke plume evacuator, but the closest the evacuator orifice in this known evacuator is located, in relation to the laser treatment site, is approximately 3.8 cm, according to communications with VISX™ Incorporated technical support personnel.

Research has demonstrated that a laser smoke plume is approximately 98.6% efficiently evacuated when the orifice of the evacuator is 1.0 cm from the target site. The efficiency drops to approximately 50% when the evacuator orifice is moved to 2.0 cm. It is clear that an orifice that is maintained 3.8 cm from the treatment site is inadequate to produce an efficient evacuation of the laser plume. (Sawchuck, W. S. et al., *Infectious Papillomavirus in the vapor of warts* . . . , J. AM. Acad. Dermatol., 1989; 21: 41–49).

The above limitations in equipment presently available explain why surgeons and other health care workers consistently smell the laser smoke plume that emanates from the corneal surface when excimer laser procedures are performed with laser machines presently commercially available, for example, those sold under the VISX™ and SUMMIT trade names.

The present invention encompasses any evacuation device which can be placed in close proximity to the site of impact of any surgical laser or electrical cautery. The devices which fulfill this criteria must have vacuum openings which are disposed during use closer than 3.8 cm from the actual treatment site.

All embodiments of the invention herein also perform as efficient smoke evacuators while remaining out of the direct path of the incident laser light. An additional feature of this invention allows various embodiments to possess additional functional features that enhance the devices' utility, but do not impair the transmission of the incident laser light and which still enable efficient smoke plume evacuation. Embodiments are described which also enable surgical lasers to interact with tissues under different fluid mixtures.

Several practical embodiments of the new evacuator device are described hereafter. The various structures all share the common ability to efficiently evacuate the smoke plume generated from a laser impact upon human or animal tissue. For the sake of discussion, excimer laser ablation of the cornea will be utilized as an example, but it is to be understood that the new device is also applicable to any other surgical procedure, such as cauterization in the usual manner, that produces a smoke plume that enters the atmosphere above (exterior of and adjacent to) the surgical treatment site.

Thus, although the term "laser" is used throughout this document, it is to be understood that in most cases the procedure under discussion could also be other types of procedures, particularly surgical procedures, which cause the production of smoke. Thus the specification and claims are not to be interpreted as limited strictly to laser surgical procedures.

The new devices disclosed herein are preferably disposed with vacuum apertures closer to the treatment site than 3.8 cm. Ideally, the apertures should be as close as possible to the treatment site while not impairing the function of the laser. While the new evacuators will function at a distance greater than 3.8 cm, closer placement is necessarily preferred for optimal smoke removal. Such closer placement is not possible with evacuators known in the art. Precisely how much closer the new device may be positioned will depend on a number of factors, including, for example, the type of surgery being performed and the skill of the particular surgeon, as well as the area of the body upon which laser treatment is imposed.

In addition to being closer than 3.8 cm, it is preferred to evacuate the smoke plume from more than one aperture to increase efficiency and to draw the laser smoke away from the treatment site in a fashion that does not draw the smoke over one part of the corneal surface more than over another part.

If an evacuation device with only a single aperture is used, as repeated laser pulses strike the corneal surface, smoke being evacuated will cross the cornea in only one direction, i.e., from one side of the eye under treatment to the opposite side thereof; i.e. smoke is drawn in an uneven distribution across the surgical site and physically interferes with the fluence of the laser light upon the cornea, such that an area with greater smoke concentration will receive less laser light because the smoke itself absorbs some of the laser energy.

By using the new evacuator with numerous apertures circumferentially located around the cornea, laser generated smoke is drawn directly toward the closest aperture and not across the cornea. In other words, the smoke is drawn radially outwardly from the inner portion (approximate center) of the surgical site, within a hypothetical perimeter established by the evacuator body portion of the device. This technique will improve reliability of the excimer laser and provide a more predictable surgical outcome by preventing smoke from crossing the path of the laser.

A commercially available aspirating speculum is available and referred to as the McBratney aspirating speculum, shown on page 248 of the Storz® Ophthalmic Instruments catalog at number E4117. This device has suction tubes connected to both arms of an eyelid speculum. However, the arrangement of apertures makes the device unsuitable for the present purpose of smoke plume removal. Rather, the McBratney speculum is structurally designed for removal of fluids from the surface of the eyeball during surgery. The holes are positioned inside the upper bend, to the left and right of center on the ends of the rigid 21 gauge metal tubing of which the speculum is made, two holes per arm. The McBratney speculum holes are filed to a size of 0.016 inches, much smaller than is necessary to accomplish the present purpose of efficient smoke plume removal.

Excimer laser companies have attempted blowing clean nitrogen gas across the cornea during excimer laser corneal treatments. The theory behind this was that by blowing nitrogen across the cornea, the laser generated smoke would be removed from the pathway of the incident light and thereby create improved uniformity in the fluence of the laser light upon the cornea. The use of nitrogen blowing was abandoned when the clinical outcomes were determined to be less desirable than when no Nitrogen blowing was utilized.

One possible reason for this decrease in the quality of the clinical outcomes may be explained by the fact that the nitrogen was blown in only one direction, entirely across the cornea, as opposed to being introduced evenly and circumferentially as is possible with some of the embodiments described herein.

As explained hereafter, another potential cause for past problems with nitrogen blowing may be due to the facts that nitrogen is an intrinsically inert gas and that the atmosphere contains approximately 21% oxygen. Interaction of an excimer laser with the cornea produces a photochemical disruption of the molecules comprising the cornea. It is not clear what changing the partial pressure of the gases in the atmosphere would have upon the nature of this photochemical reaction, but considering that oxygen is a reactive molecule and that the excimer laser impact has been demonstrated to be an explosive phenomenon (Puliafito, C. A., et al., Arch Ophthalmol. 1987; 105:1255–1259), control over the concentration of potentially reactive gases in the air space above the laser impact site is considered to be important to obtaining predictable, reliable results with any laser surgery, e.g. excimer laser surgery.

With the present invention, the vacuum produced by the smoke plume evacuator can be configured to efficiently remove the generated laser smoke in exchange for clean room air, leaving the partial pressure of the air mixture above the treatment site unchanged. Furthermore, another embodiment of this invention allows for simultaneous evacuation of the laser plume and circumferential delivery of any clean fluid mixture into the laser path which may be more desirable for laser-tissue interaction (for example, a reactive atmosphere containing a partial pressure of oxygen of 25% as opposed to 21%).

During excimer laser corneal surgery, it is customary to place an eyelid speculum into the cul-de-sacs (engaging and/or under the lids) of the eye. This is done so that the patient cannot blink during the treatment process. In one embodiment of this invention, a lid speculum is configured with an integral smoke plume evacuator so that this device addresses a need that already exists in standard excimer laser surgery. Other embodiments are disclosed herein which serve multiple purposes but which alter the already somewhat established protocol for excimer laser treatments.

In some embodiments of this invention, a lid speculum is configured with a smoke plume evacuator so that the new device can simultaneously keep the eyelids open while efficiently removing the laser smoke plume. The apertures of this lid speculum are preferably disposed in normal use position less than one centimeter from the treatment site and as such can be optimally efficient in removing the laser smoke plume.

Because a lid speculum is a standard device utilized for excimer laser surgery, this device will perform two functions at the same time. The evacuated smoke plume can be routed into the standard filtration system that is present on the VISX™ Star Excimer Laser System™, or routed to a standard commercially available evacuation system with appropriately replaceable filtration systems. The nature of the commercially available filtration system is well known.

Finally, for the lid speculum design, one embodiment would contain an additional set of tubing that would be stacked upon the plume evacuator tubing. This additional set of tubing can be used to bring in clean gas or other fluids or mixtures thereof which are different from atmospheric (ambient) gas. This process enables the laser to interact with tissue under a fluid environment which is different from atmospheric gas and which may allow for an improved laser-tissue interaction.

Another embodiment of this invention is an ocular fixation device which comes in contact with the conjunctiva around the cornea. One design that is considered is similar to the Fine-Thornton fixation ring as sold by Rhein Medical, Inc. This device has a handle suitable for manually controlling the device. The portion which contacts the patient's eye is an incomplete circle with small teeth to engage the conjunctival surface. In this embodiment, the portion of the fixation ring just above the part that contacts the conjunctiva can be a tube with one or more apertures, which tube leads to a filtration vacuum system which is appropriate for receipt of biohazardous materials for disposal thereof.

In use, this embodiment of the new device is placed against the conjunctiva around the cornea to assist in the fixation of the eye for surgery, and the vacuum, when activated, enables efficient smoke plume evacuation preferably at a distance approximately 1.0 cm or less. With the fixation ring embodiment, an additional circle of tubing can be attached to the fixation device so that different gas mixtures can be delivered to the treatment site and enable potential modifications of the laser-tissue interaction.

Other embodiments of this invention are conceived whereby a structure with one or more apertures is placed against the eyelid skin hovering over the cornea. With this embodiment, a standard eyelid speculum could be utilized. This tubing, with one or more apertures, could have small vertical extensions which then contact the skin and enable the surgeon to hold this in place in close proximity to the treatment site. This device will have a greater distance from the treatment site than either the lid speculum embodiment or the fixation ring embodiment but will still provide a level of smoke plume evacuation efficiency which is greater than that which is currently available in the VISX™, Incorporated or Summit Technology, Inc. lasers. This embodiment can also incorporate a separate ring of tubing which can introduce different gas mixtures to the space above the treatment site.

One of the ways in which the fixation embodiment of the device disclosed herein is useful is for surgery on other body surfaces, when those surfaces are receiving various laser treatments. One example of this is the laser removal of virally produced condyloma of the genital tract. In this fashion, the condyloma to be treated are located within the circular fixation ring which holds the skin taut, while the laser treatment is delivered efficiently through the central aperture of the fixation ring. Also during this treatment, the smoke that is generated is efficiently removed because of the very short distance between the laser tissue interaction site and the apertures of the smoke evacuation system.

Another site for potential use is the cervix. Collins has described a vaginal speculum which is partly connected to a vacuum suction device. The intention of that device is to remove smoke from the vaginal vault during cervical laser treatments or other smoke producing procedures. The Collins patent does not teach any important distances from the source of the smoke, and as such the embodiments described in that patent do not provide for an efficient smoke removal system, as does the present devices.

In the present invention, a standard vaginal speculum is inserted and a long handled fixation device connected with tubing inserted into the vagina with the circular fixation ring being brought against the uterine cervix to hold it steady, to manipulate it during treatment, and, most importantly, to evacuate any smoke generated from this tissue during laser or other smoke producing procedures. This function for the fixation device is better than the Collins device in that improved visualization and more efficient smoke evacuation can occur because of the greatly shortened distance between the laser tissue interaction and the apertures of the smoke evacuation tubing.

The embodiment for cervical treatment is therefore ordinarily expected to have a longer fixation handle than that used upon the eye, and the distal fixation ring would have to be of larger diameter than that used on the eye. A reasonable useful range of diameters is considered, for example, a 2.5 to 3.0 cm diameter ring-shaped evacuator body is appropriate for treatment of the uterine cervix. Similarly, any other surface or body cavity which requires an efficient evacuation of smoke from the interaction of laser or other cautery devices with tissue could be utilized with appropriate modification of the speculum, fixation device or smoke evacuation tube of the new evacuation device.

As mentioned elsewhere herein, an independent, but connected tubing can be arranged such that one set of tubing is used for efficient close range smoke evacuation, while the other is used for the importation of any desired air/gas mixture, or liquid (fluids). If liquid is introduced through the second set of tubing, the vacuum present on the second set of tubing can double as a liquid evacuator as well. If the fixation device is used in the vagina, other baffles or structures can be affixed to the fixation handles, as may be necessary to assist in keeping vaginal tissues out of the direct path of the laser.

Although possibly unnecessary, the present device is considered a conduit for these procedures, such that even a conventional light pipe could be introduced down the handle to facilitate the view of the cervix for appropriate treatment with the laser.

Accordingly, it is among the many goals and advantages of the present invention to provide a surgical smoke plume evacuation device which may be integral with or detachably connected to a speculum for use in surgical treatment of tissue with a laser, electrical cautery or other smoke plume causing device. Various embodiments of the new device are appropriate for different tissues, at different areas of the body and can be used with a variety of types of speculums.

It is further among the many goals and advantages of the device having the features enumerated above, that it can be made of materials that are relatively inexpensive and disposable, or alternatively may be sterilizable for reuse and may be adapted for introduction of fluids into the area ambient to the surgical site.

It is still further among the many goals of the invention to provide a device which can be used by an already skilled professional in the art with little or no additional training or practice prior to use on a patient, which device will protect the surgeon, the patient and other individuals in the vicinity of a surgical procedure from any potentially hazardous substances that may be in a smoke plume produced during the procedure, and that such device will thereby assist medical facilities in meeting OSHA and ANSI standards for safety in work places using laser surgical procedures.

Accordingly, in furtherance of the above goals, the present invention is, briefly, a surgical laser smoke plume evacuator which includes an evacuator body formed to a shape which is suitable for placement in normal use position substantially entirely around and adjacent to a tissue site upon which laser surgery is to be performed. The evacuator body has structure for removing smoke therethrough, and a smoke exit portion in communication with and extending from the evacuator body. The smoke exit portion is connectable to vacuum source, to thereby apply a vacuum to the evacuator body and cause smoke which is created at a surgical site during surgery to be removed from the surgical site through the evacuator body and the smoke exit portion.

The invention is also, briefly, the combination of an eyelid speculum and a surgical laser smoke plume evacuator device, wherein the smoke plume evacuator device includes an evacuator body which is formed to a shape which is suitable for placement in normal use position substantially entirely around and adjacent to a tissue site upon which laser or other smoke producing surgery is to be performed. The evacuator body has structure for removing smoke therethrough. A smoke exit portion is in communication with the evacuator body, and extending away from the evacuator body, the smoke exit portion is connectable to vacuum source, to thereby apply a vacuum to the evacuator body and cause smoke which is created at a surgical site during surgery to be removed from the surgical site through the evacuator body and the smoke exit portion.

Further in the combination, the evacuator body of the smoke plume evacuator device is formed of tubing and the structure for removing smoke therethrough is a plurality of openings spaced around an internal aspect of the evacuator body and extending from a luminal surface of an internal aspect thereof to a nonluminal surface thereof, at least some of the plurality of openings being disposed less than 3.8 cm from a point of smoke producing surgical contact with tissue of the surgical site.

The invention is further, briefly, a method of removing a smoke plume created during surgery. The new method includes selecting a smoke plume evacuator device having an evacuator body and a smoke exit portion in communication with the evacuator body, positioning the evacuator body of the surgical smoke evacuation device around a surgical site so that the site is accessible via an inner aspect of the evacuator body, and so that at least some structure on the evacuator body inner aspect for removing smoke are disposed less than 3.8 cm from the smoke producing surgical treatment site, connecting the smoke exit portion of the evacuation device to a vacuum source, applying a vacuum to the smoke exit portion of the evacuation device, and initiating a smoke producing surgical procedure upon tissue at the surgical site, the smoke being produced exiting radially away from the surgical site via the structure for removing smoke on the evacuator body and then via the smoke exit portion toward the vacuum source.

These and other advantages and features of the invention will be in part apparent and in part pointed out hereinbelow.

BRIEF DESCRIPTION OF THE DRAWINGS

FIG. 1 is a perspective view of a surgical laser smoke plume evacuator constructed in accordance with the invention.

FIG. 2 is a top plan view of the device of FIG. 1, shown in position for use on a patient's eye.

FIG. 3 is a perspective view of an alternative embodiment of the surgical laser smoke plume evacuator device of FIG. 1, adapted for the introduction of extraneous fluids to the surgical site.

FIG. 4 is an elevational view of the device of FIG. 3, taken from the end positioned at the left side of FIG. 3.

FIG. 5 is an elevational view of the device of FIG. 3, taken on line 5—5.

FIG. 6 is a perspective view of another embodiment of the surgical laser smoke plume evacuator device of the present invention, mounted to a rigid fixation type speculum.

FIG. 7 is a perspective view of an alternative embodiment of the device of FIG. 6, adapted for introduction of extraneous fluids to the surgical site.

FIG. 12 is an elevational view of the device of FIG. 11, taken from the end shown at the left in FIG. 11.

FIG. 13 is a perspective view of a still further embodiment of the evacuator device of the invention, shown in phantom for clarity of the drawing and connected to a modified wire, retractor type eyelid speculum.

FIG. 14 is a perspective view of another embodiment of evacuator device constructed in accordance with the present invention.

FIG. 15 is a top plan view of another embodiment of the evacuator of the present invention, shown in position over an eye, as in normal use position.

FIG. 16 is a perspective view of an alternative to the embodiment shown in FIG. 15.

FIG. 17 is a perspective view of another alternative to the embodiment shown in FIG. 15.

FIG. 18 is still another embodiment of a surgical smoke plume evacuator constructed in accordance with the present invention.

FIG. 19 is a perspective view of an alternative to the embodiment shown in FIG. 18, adapted for introduction of extraneous fluids to the surgical site.

Throughout the drawings, like parts will be indicated by like element numbers.

DESCRIPTION OF THE PRACTICAL EMBODIMENTS

Figure 10:
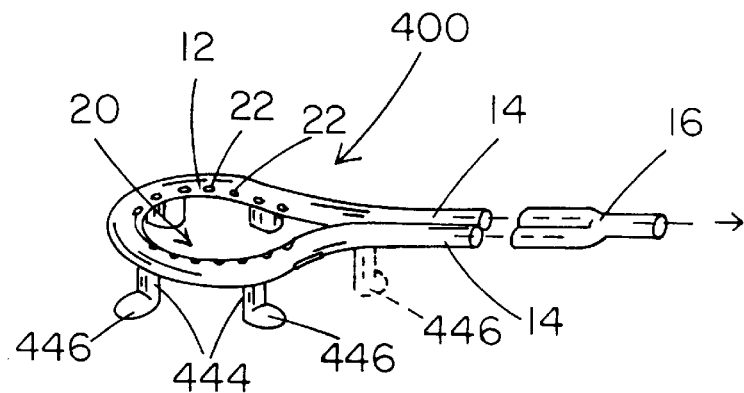
FIG. 10 is a perspective view of a still further embodiment of the surgical laser smoke plume evacuator constructed in accordance with the present invention.

With reference to the drawings, and particularly with reference to FIGS. 1 and 2, 10 generally designates a smoke plume evacuator constructed in accordance with and embodying the present invention. All embodiments of the new device are preferably formed, most basically, as a loop of medical grade tubing with a series of formed holes (or apertures) facing the inside of the loop, i.e. on the luminal aspect from the nonluminal surface entirely through to communicated with the lumen of the tubing, and with the ends of the section of tubing being placed, generally, together, and usually directed away from the area surrounded by the apertured, curved wall of the tubing.

Smoke plume evacuator 10 includes an evacuator body portion 12 and paired vacuum or suction tubes 14, extending distally therefrom in use, approximately parallel to each other, for attachment to a known vacuum source (not shown) via an appropriate conventional connector, such as "Y" connector 16. Smoke exit tubes 14, when positioned parallel to each other, as shown, can be secured to each other by any reasonable means, for example by one or more bands, such as indicated at 15, clips, "welding", gluing, etc., for improved stability of the entire unit 10.

Evacuator body portion 12 is usually formed from a known type of commercially available, medical grade tubing into a generally oval shape for placement around an eye E to be subjected to laser surgery. Preferably the outer diameter of the tubing selected is in the range of about 2.0 to about 4.0 mm and the inner diameter is in the range of approximately 0.5 to approximately 3.0 mm.

Body portion 12 is mounted on flat extensions or wings 18. Wings 18 are preferably of a type known in the ophthalmological surgical art, formed of a surgical grade plastic, and ordinarily sized in the range of about 1.0 to about 2.5 cm in length and from about 0.5 to about 1.5 cm in width. When so mounted on wings 18, as by gluing, or heat sealing, for example, the open area 20 defined by evacuator body portion 12 is about 12 to about 25 mm wide and about 1.5 to about 3.0 cm long.

FIG. 2 illustrates evacuator 10 positioned above an eye E for use, with wings 18 disposed beneath the conjunctiva C of the eyelids, and with evacuator body portion 12 pushing back the lashes of eye E. Evacuator 10 thus, in this embodiment, functions as both a speculum and a smoke evacuator, when suction is applied through apertures 22 during laser surgery.

Critical to proper functioning of evacuator 10 is the provision and positioning of a plurality of smoke suction apertures 22, spaced apart on the inner wall of body 12 which forms the perimeter of area 20. Apertures 22 are desirably approximately 0.5 to 3.0 mm in diameter, and may be of any shape, most probably round, or somewhat oval, when the tubing of body 12 is disposed in normal use position on wings 18. In order for device 10 to function as intended, apertures 22 are disposed on the wall of body 12 so as to be directed substantially level with or just above the air space in a plane just above the surface of the eyeball E being subjected to laser treatment.

It should be understood that a plurality of apertures 22 is preferred for the most efficient evacuation of the smoke plume. However, it is conceivable that a single aperture 22 of sufficient size and located less that 3.8 cm from the point of production may suffice and is better than any currently available mechanisms.

In this manner, the smoke plume generated by tissue/laser interaction can be most quickly and efficiently removed from the work area, by withdrawing it through apertures 22, in at least two directions, away from the surgical site, as illustrated by the arrows in FIG. 2. This technique prevents smoke from being dragged across the worksite, through the laser field, by the vacuum force that would be applied by having only one aperture.

The above-described preferred dimensions of tubing and apertures are the same for all embodiments of the invention described hereafter. Throughout the following description of various embodiments, parts which are identical with corresponding parts in other embodiments will be designated with the same element number. The various embodiments, however, and parts which varying among them will be provided with different elements numbers.

FIGS. 3–5 illustrate a second embodiment of a smoke plume evacuator device 100, which is the same as that shown in FIGS. 1 and 2, except that a second layer of tubing is applied over and fixed to the first layer, i.e., evacuator body 12, with apertures 126 spaced along the wall forming the inside of the curve, to form a fluid influx body 124. Tubules 128 extend distally during use from influx body 124 to a source, such as a gas canister (not shown) of the fluid to be introduced.

Apertures 126 and the tubing of influx body 124 may vary in size from those described above, with reference to the first embodiment, as may be necessary to accommodate a particular fluid, such as a gas, other than air, or possibly even a liquid, to be introduced to the work site, for reasons described previously. Otherwise, the structure of fluid influx body 124 can be the same as that described for smoke evacuator body 12.

If the fluid influx and vacuum lines should be accidentally interchanged, no harm would be done to the patient. Indeed, there conceivably are procedures wherein it is preferred by the surgeon to intentionally cross the influx and vacuum lines, so that fluid is introduced at the level closest to the operative surface and smoke is evacuated from the level of the new device further from the tissue, i.e. from the upper tubing ordinarily intended for and described herein as the fluid influx or introduction body.

FIG. 6 illustrates a third useful embodiment of the new smoke plume evacuator, generally designated 200, and consisting of a similar tubing loop form of evacuator body 12 as in the first embodiment, with suction apertures 22 and paired distally directed extensions 14. However, in this embodiment, the tubing of the body 12 and extensions 14 are connected to rigid speculum 232 of known type, with teeth 234 for fixation to the operative tissue extending from one side of a fixation ring 235, opposite the side upon which evacuator body 12 is affixed.

Ring 235 is preferably rigid and permanently attached to evacuator body portion 12, for example by heat sealing or gluing, or other appropriate means. Alternatively, ring 235 could be detachably connected to body 12, for example by bands, clips, etc. As a still further alternative, in this embodiment, ring 235 could be formed of a soft metal or plastic, so as to be somewhat flexible; or the ring could be omitted altogether, and teeth 234 could then be formed on or connected by any appropriate means to the side of body 12 which is proximal in use.

Teeth 234 are preferably generally triangular in shape, pointing toward the tissue to which the speculum is to be detachable fixed, and are approximately 0.25 to about 1.0 mm long and about 0.1 to approximately 1.0 mm wide. Teeth 234 are shown exaggerated in the figures, for clarity. Alternatively, teeth 234 could be formed more as smooth bumps or ridges, rather than as more sharply formed teeth, as shown.

An optional speculum handle 238 extends, as shown, distally from fixation ring 235 and can serve to support evacuation tubing extensions 14. Handle 238, as in other embodiments with speculum handles, can be omitted entirely, or can be shaped to suit the user's needs, i.e., other than as shown.

Figure 8:
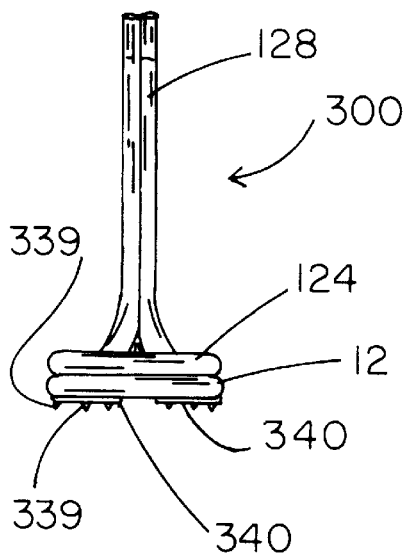
FIG. 8 is an elevational view of the device shown in FIG. 7, taken from the end shown at the left side of FIG. 7.
Figure 9:
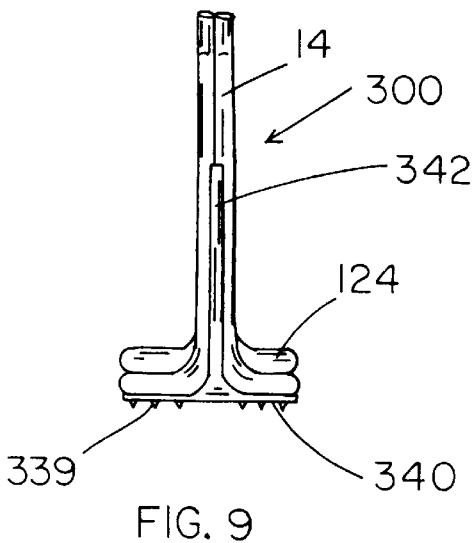
FIG. 9 is an elevational view taken from the opposite end as that shown in FIG. 8.

FIGS. 7–9 illustrate a smoke plume evacuator, generally designated 300 which is a variation on the embodiment shown in FIG. 6. Evacuator 300 has an evacuator body 12 with extensions 14, as well as the second layer of tubing which forms an influx body 124, just as in the embodiment shown in FIGS. 3 through 5. Evacuator 300 is also mounted on a rigid fixation speculum 338, similar to that shown in FIG. 6, with teeth 339 substantially the same as teeth 234 in FIG. 6. However, in this case, the fixation ring 340 is shown as a variety which is split at its most proximal end, generally opposite the point of attachment of handle 342, as seen most clearly in FIGS. 8, as opposed to the closed ring variety used in FIG. 6.

It should be understood that speculums 232 and 338 could be interchanged between the embodiments of FIGS. 6 and 7, with respect to whether they are used to mount an evacuator alone, or in combination with a fluid influx tubing. As with the embodiment shown in FIGS. 2–4, the smoke plume is evacuated via the connection of known vacuum means by connector 16 to distal tubules 14, and optional influx of fluids is accomplished via connection of distal tubules 128 with connector 130, for example, to a conventional source of fluid (gas or liquid, as desired by the surgeon or required for a particular procedure).

Also, it should be understood that although the use of conventional Y connectors to fluid lines is illustrated, the same purpose can of course be accomplished by other known connection means, for example, by multiple single connectors, to multiple lines, or by use of known types of valving arrangements, as however may be suitable for the medical procedure being performed.

FIG. 10 illustrates an alternative embodiment of the new smoke plume evacuator, generally designated 400. Evacuator device 400 has an evacuator body 12 and paired, parallel tubular extensions 14 therefrom, just as in the first embodiment. However, instead of being mounted on an eyelid speculum of the winged type 18 shown in FIG. 1, device 400 is supported by a plurality of leg structures 444, preferably four in number, as shown, but conceivably three, or more than four, spaced about the extent of body 12.

Optionally, at least one additional leg 444 and foot 446 structure, such as that shown in phantom in FIG. 10 can be provided under the evacuation tubes 14 to provide support and ameliorate a potential need for extraneous support, for example by a hand of such distally extending tubes 14. This feature can of course apply to other embodiments as well.

Leg structures 444 each preferably have a foot 446 disposed substantially perpendicularly at the lower end of the leg, to rest upon the skin surrounding the eye, or other tissue surface to be subjected to laser or otherwise cauterizing surgery. Optionally, the end of the leg, whether footed or not, can be provided with a sticky substance to enhance the ability of the device 400 to remain in the desired use position. Surgically acceptable sticky substances are well known and commercially available.

Indeed, it is conceivable that the evacuator body portion, could be provided with a surgical grade sticky substance (not shown) applied to the skin side surface thereof, covered by a peel-off protector sheet until use, to thereby removably attach the evacuator device to the skin surface around the eye, or other outer body surface upon which device 400 (or other embodiments of the invention) are to be used.

In the preferred structure, legs 444 are each formed to be about 0.5 to about 1.5 cm high and the feet, for optimal stability, are approximately three to about 10 mm in both width and length.

As examples only, the device 400 can be used in combination with a separate, independent eyelid speculum of any suitable variety (not shown), or placed so that the area 20 defined by the perimeter formed of evacuator 12 is directly over, for example, a mole, or other tissue to be surgically removed by laser or electrical cautery. In either case, the spaced apertures 22 would be disposed around and above the surgical site for optimal removal of surgically generated smoke.

Figure 11:
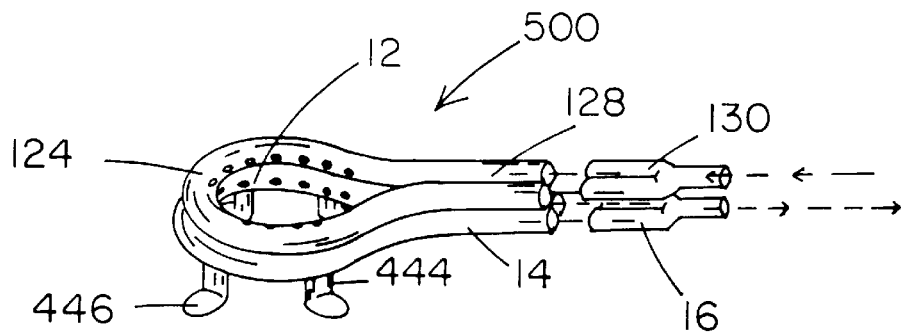
FIG. 11 is a perspective view of an alternative to the embodiment shown in FIG. 10, adapted for introduction of extraneous fluids to the surgical site.

FIGS. 11 and 12 illustrate a variation on the embodiment of FIG. 10, wherein evacuator device 500 is substantially the same as device 400, but has an additional overlying body 124 and extension tubes 128 connected by connector 130 to a conventional source (not shown) of in-flowing fluid. This aspect corresponds to the alterations shown in evacuator 100 (FIGS. 3–5) as compared to the first embodiment, in FIG. 1. However, evacuator 500 also is endowed with leg and feet structures 444/446, as in evacuator 400 (FIG. 10).

FIG. 12 illustrates that legs 444 have perpendicular flanges 445 upon which the proximally directed surface of body 12 is fixed, for example by gluing, heat sealing, or by any other means appropriate for use with a surgical device.

FIG. 13 illustrates a further alternative embodiment of the new smoke evacuator device, generally designated 600. In this embodiment the evacuator body 648 is shown partly in phantom, for clarity of the figure, and the speculum to which it is connected, generally designated 650, is illustrated schematically, in solid lines.

Smoke evacuator body 648, as shown in FIG. 13, has two independent arms 652, each with an end 654 which is directed proximally in use, the two ends 654 substantially facing one another, but separated as shown, and both being occluded, as, for example, by heat sealing or plugging, to prevent pulling air through ends 654 when a vacuum is applied to remove the surgical smoke plume. Spaced apertures 656 are formed at spaced intervals along the inside curvature of each arm 652 of evacuation body 648 for purposes of withdrawing the smoke plume created during surgery.

In all embodiments, the size and positioning of the evacuation apertures is appropriate for the function of sucking smoke from the air space just outward from the surgical site. The apertures are not positioned downwardly or otherwise for removal of liquids from the actual surface of the eye or other tissue being subjected to the procedure.

As with the embodiment shown in FIG. 1, the proximally directed extensions 658 connect, preferably by a Y-connector 16 to a conventional vacuum source. However, the speculum 650, varies greatly from the winged version shown in FIG. 1. In this embodiment, speculum 650 is of a wire, spring-type, for example a modification of existing styles, such as that presently marketed as a Simcoe eye speculum by Storz Ophthalmic Instruments.

The modified speculum 650 of this embodiment preferably has paired, substantially parallel extensions or arms 660 disposed above and below the surgical site. To each extension 660 is affixed a longitudinally extending lower loop 662 which is curved downwardly and away from the site, to receive and retain an eyelid on the corresponding side of the site, during the procedure.

Curving upwardly and away from the central surgical site and fixed to each of the two extensions 656, spacedly therealong, are preferably a plurality of upwardly and outwardly curved retaining fingers 664 into which a corresponding tubular arm 652 of evacuator body 648 is detachably introduced. Thus, with this embodiment, the evacuator body 648 can be removed and disposed of after a procedure, and the speculum portion 650 can be cleaned, sterilized and reused. Alternatively fingers 664 can be continuous with evacuation tube arms 654 permanently mounted therein. In that case, however, the entire device 600 would probably be disposed of after a single use, rather than reusing the speculum portion 650.

Although lower loops 662 and upper fingers 664 on speculum arms 660 are most likely to be formed of metal wire, either or both could also be formed of other materials and still function suitably. For example, the curved portions 662, 664 can be formed of thin curved sheets of plastic or metal. Also, the entire speculum 650 could be formed of plastic.

FIG. 14 illustrates a still further embodiment of the invention, generally designated 700. In this version of the new evacuator, the evacuator body 766 is composed of a single loop of tubing, having one end 768 occluded and looped around, to a point touching, or adjacent, as shown, to a single distally extending tubule 770. Evacuator body 766 is preferably looped in an oval shape, much as in the first embodiment, but terminates in occluded end 768, rather than having two distally extending evacuation arms 14 as in the first embodiment.

Of course, as with the other embodiments, the general shape outlined by the tubing of evacuator body 766 can also vary, although it is expected that a generally oval shape is optimal for use in eye surgery as it conforms to the usual shape of the opening formed by the eyelids.

Smoke evacuator device 700 is also provided with a base 772 for supporting the preferably flexible tubular body portion 766. Base 772 may take many reasonable forms, but preferably, as shown, is a thin sheet of sterilizable plastic, formed into a winged shape the same as or similar to that of which wings 18 in the first embodiment are formed. Thus, base 772 acts as an eyelid speculum, as do the wings of the first embodiment.

Also, base 772 serves the additional function of supporting evacuator 700, and therefore does not have to be used in conjunction with an independent eyelid speculum. If desired, the plastic film forming base 772 can be trimmed by surgical scissors to another size or shape, and still retain the function of providing support to the flexible tubing of evacuator body portion 766.

A plurality of evacuation apertures 22 are spaced along body 766 and are the same as in the first embodiment, but the curved length of tubing forming body 766 is optionally retained in its position upon base 772 by curved pieces 774, connected (for example, by gluing) at spaced intervals around the inner edge of the base, as shown in FIG. 14. Alternatively, base 772 can be glued, heat sealed, or otherwise appropriately mounted to the side of the tubing which will face the surgical site.

In the last described embodiment, only a single connector, such as that indicated at 771, for example is necessary to attach smoke exit tube 770 to a vacuum line.

FIG. 15 illustrates a further configuration, generally designated 800, conceived for the new smoke evacuation device. Variations on this design are shown in FIGS. 16 and 17, and are generally designated 810 and 820, respectively. Evacuation device 800 (FIG. 15) is shown in normal use position over eye E, with side wings 18 beneath the conjunctiva C, as in the first embodiment, shown in FIGS. 1 and 2. However, this design varies from the first in that evacuator body portion 876 is not a complete loop, but, like portion 648 of the embodiment depicted in FIG. 13, has two curved arms, each having a proximally directed end 880 which is sealed, or otherwise occluded and extends generally toward, but is spaced apart from the corresponding end of the other arm 878.

The vacuum apertures in each arm 878 are substantially the same as those found in all other embodiments. However, a further difference in this embodiment is the provision of only a single distally extending tubule 882 for evacuation therethrough of the smoke plume which is suctioned in from the surgical site through apertures 22. Rather than attachment to vacuum means by a Y-connector as in most of the previous embodiments, tubule 882 can be connected by any conventional appropriately sized and shaped tube connector (for example, such as that indicated at 771 in FIG. 14).

The embodiments shown in FIGS. 16 and 17 share some of the characteristics of various previous embodiments. Evacuator 810 (FIG. 16) includes paired distally extending evacuation tubules, as in the first embodiment, but has an evacuation body portion 876 like that described and shown in FIG. 15, with paired curved arms 878, each having a closed (occluded) end 880.

FIG. 17 shows an embodiment having evacuation stem or tubule 882, like that shown in FIG. 15, but the evacuator body portion 12 is the same as that shown in the first embodiment, in FIGS. 1 and 2, with a closed loop structure. Like evacuation device 800 in FIG. 15, here the distally directed end of the two parts (above and below the eye in the figure) of the body portion (on the left side in each figure) come together to form a Y as an integral part of the structure, rather than extending away from the body portion as two independent tubules (as in device 810, in FIG. 16). Thus, a Y-connector or other connection device is necessary to unite the two separate smoke exit tubules before connecting to a single vacuum source. (The use of two independent vacuum sources or lines to one vacuum source are possibilities which are considered to be less practical).

FIGS. 18 and 19 illustrate still further practical embodiments 900 and 910, respectively, sharing various combinations of features shown and described with reference to the previous embodiments. Smoke evacuator device 900 (FIG. 18) has in common with the embodiment of FIG. 6 a closed loop style evacuation body portion 12 with vacuum apertures 22 spaced around the inside wall thereof and being mounted on a fixation ring type 232, with a preferably oval or circular base ring 235 and multiple teeth 236 for fixing the device in position around the laser operation site.

If desired, teeth 236 can be formed differently from those shown in FIGS. 6–9. For example, the teeth may be larger and formed in the range of about 1.0 to about 3.0 mm long and about 0.5 to about 2.0 mm wide at their bases.

Furthermore, in FIG. 18, the upwardly angled stem portion 984, for smoke evacuation is only a single tubule, as opposed to the double arrangement in previous embodiments. This is similar to the tubular extension 882 in the embodiment of FIG. 17, but instead is formed at sharp angle, so as to extend substantially vertically upwardly, rather than more laterally, in relation to the surgical site and to the plane in which the corresponding evacuator body lies.

As with the embodiments shown in FIGS. 6, 7–9 and 19, this smoke plume evacuator can be used for procedures other than eye surgery. For example, the angled smoke exit tube 984 provides a convenient shape for use in vaginal laser surgery, most probably in combination with the use of a conventional vaginal speculum (not shown).

The embodiment generally designated 910 in FIG. 19 includes a body portion 12 as in the first embodiment, with an overlaid, attached fluid influx tubular body 124, as shown in the embodiment in FIGS. 7–9. However, as in evacuator device 900, in FIG. 18, there is only one distally extending tubule 984 for smoke evacuation. Similarly, only one fluid influx tubule 986 is provided.

As with the previous embodiments, all constructions shown in FIGS. 15–19 are suitable and well within the scope of the invention. Which particular embodiment is selected for a certain purpose will be determined by the surgeon's preference or requirement for a particular type of speculum, or may be determined by the type of surgical procedure involved. Manufacturing considerations may cause some embodiments to be more costly than other embodiments and thus may also play a role in determining which of the constructions shown is most commonly used.

All the embodiments described above, and other foreseeable variations thereof, are preferred to be made of disposable, light-weight, inexpensive materials which are provided to the surgeon pre-sterilized, most probably in the form of a kit, packaged in a manner commonly used for surgical supplies, most likely for one-time use, to reduce any risk of transfer of infection. However, it is also within the scope of the invention that the structures described above and their equivalents be formed of metal, or other materials that can be reused after appropriate cleaning and re-sterilization, between patients, or procedures, in keeping with standard, accepted medical surgical practice.

Depending upon the materials selected, a given embodiment of the invention is sterilizable by heat, by autoclaving, or even boiling; or in some cases may be sterilized by other methods, known or to be developed, such as exposure to ultraviolet irradiation or certain liquids or gases. For example, although the preferred material for the evacuator device body and extension tubules is a soft, flexible plastic tubing, it could also be formed of a metal tubing which is at least semi-rigid, although capable of being formed to a desired shape, either during manufacture, or possibly even by the practitioner using the new device. For some procedures, however, stainless steel, or conceivably even glass may be the optimal material.

Likewise, the sizes of the elements and shape of the opening, e.g. 20 in FIG. 1, formed by the evacuator body portion can vary and still be within the scope of the invention. Although an oval shape is shown and described herein, especially with reference to use for eye surgery, it is expected, as previously explained, that the new smoke plume evacuator will be used for other types of surgery as well, and thus, maintaining the general eye shape may be unnecessary.

In some situations other shapes may be preferred, and are certainly in keeping with the invention. These shapes may include, but are not limited to, triangles, squares or other rectangles, hexagons, circles, and so one, as may be useful or desired for a particular procedure.

Similarly, the shape and type of speculum to which the new device is attached, and the means of connecting the new smoke evacuator, with or without the fluid influx attachment, can vary, as however may be desired or necessary for a procedure, the specific structures and speculums described and shown herein being intended only as useful examples, and not as limitations on the constructive designs foreseen.

It is the purpose of this invention to enable the medical community to better comply with OSHA and ANSI standards. It is clear from the medical literature that the orifice of an evacuation device needs to be 1.0 cm or closer to the point of production of a tissue smoke plume to efficiently evacuate it from the treatment site. In the present invention, several strategies are taught which facilitate plume evacuation to a degree which exceeds that currently available in the medical field; this will empower the medical community with instrumentation which will facilitate the fulfillment of OSHA and ANSI regulations to the highest order.

In view of the foregoing, it will be seen that the several objects of the invention are achieved and other advantages are attained.

Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description or shown in the accompanying drawings shall be interpreted as illustrative rather than limiting.

What is claimed is:

1. A device for evacuating smoke which is created by contact of a surgical laser with tissue the device comprising:
   an evacuator body which is formed to a shape which is suitable for placement in normal use position substantially entirely around and adjacent to an area of tissue upon which laser surgery is to be performed, the evacuator body defining a perimeter of the area of tissue and having structure for removing smoke therethrough, the structure for removing smoke therethrough lying in a plane adjacent to and distal to the area of tissue;

a smoke exit portion in communication with the evacuator body, and extending from the evacuator body, the smoke exit portion being connectable to a vacuum source, to thereby apply a vacuum to the evacuator body and cause smoke which is created during surgery by contact of the surgical laser with tissue to be removed from the area of tissue through the evacuator body and the smoke exit portion;

wherein the evacuator body comprises two pieces of tubing each having a proximal end and a distal end in normal use position and, arranged adjacent to each other, but curving outwardly, away from each other and then inwardly, toward each other at proximally disposed free ends thereof to provide a perimeter substantially entirely around a surgical site, each of the free ends being occluded so that the application of a vacuum to the device will cause a vacuum to be pulled through the structure for removing smoke from the evacuator body, and each of the two pieces of tubing having a distally disposed end in normal use position, the distally disposed ends forming the smoke exit portion and being connectable to a vacuum source and the structure of the evacuator body for removing smoke therethrough comprises a longitudinal axis which is nonperpendicular to the tissue being treated and a plurality of openings disposed on an internal aspect of the evacuator body and extending from a luminal surface of the internal aspect of the evacuator body to a nonluminal surface thereof, and facing inwardly, toward the area of tissue upon which laser surgery is to be performed;

wherein the plurality of openings are spaced apart from one another along the tubing forming the evacuator body; and the evacuator body is appropriately sized and shaped, so as to be capable of being operatively disposed around the tissue area with a point at which the surgical laser is to contact the tissue in the tissue are positioned less than 3.8 cm from at least one of the plurality of openings.

2. The device of claim 1, wherein the plurality of openings on the evacuator body is at least a first opening and a second opening, the first opening being disposed substantially opposite and facing the second opening.

3. The device of claim 1, wherein the evacuator body is formed of tubing and the smoke exit portion is at least one tubule which is integral to and in communication with the evacuator body.

4. The device of claim 1, wherein the smoke exit portion is formed of a pair of tubules disposed substantially parallel to one another.

5. The device of claim 4, and further comprising at least one connector connecting the pair of tubules forming the smoke exit portion to one another, to thereby retain their substantially parallel relationship.

6. The device of claim 5, and further wherein the pair of parallel smoke exit tubules are connected by a Y-connector to a vacuum source.

7. The device of claim 1, and further comprising support structure connected to the evacuator body to thereby maintain the evacuator body in an operative position relative to the tissue at the surgical site.

8. The device of claim 7, wherein the support structure includes a plurality of teeth spacedly disposed along the extent of and connected to a lower aspect of the evacuator body.

9. The device of claim 7, wherein the support structure is a rigid ring connected to a lower aspect of the evacuator body.

10. The device of claim 7, wherein the support structure is a plurality of legs spacedly connected to the evacuator body, around a lower aspect thereof, the legs being supported in the normal use position upon a skin surface surrounding the surgical site, to thereby support the evacuator body in a preselected raised position substantially surrounding and adjacent to the surgical site.

11. The device of claim 10, wherein the plurality of legs is at least three legs.

12. The device of claim 11, and further comprising at least one additional leg under distally directed smoke exit portion.

13. The device of claim 7, wherein the support structure is of the rigid fixation type, and further wherein the evacuator body is supported by a fixation ring of the support structure and the smoke exit portion is supported at an angle relative to the evacuator body by a handle of the support structure.

14. The device of claim 7, wherein the support structure is a speculum.

15. The device of claim 14, wherein the speculum has at least one arm and at least one finger structure mounted to the at least one arm, the at least one finger structure extending at least substantially entirely around a portion of the evacuator body, to thereby receive and retain the portion of the evacuator body until the portion of the evacuator body is selectively separated from the speculum arm.

16. The device of claim 15, wherein the at least one finger structure is a plurality of finger structures, upwardly and outwardly directed from the speculum arm to which they are fixed, to retain the evacuator body in a normal use position.

17. The device of claim 14, wherein the speculum is a retractor type and formed at least in part of plastic.

18. The device of claim 14, wherein the speculum is fixed to the evacuator body.

19. The device of claim 14, wherein the speculum is made of sheet-like material and formed to an appropriate size and shape so as to be insertable beneath the conjunctiva of an eye at the surgical site.

20. The device of claim 14, wherein the speculum includes structure to selectively detachably connect the speculum to the evacuator body.

21. The device of claim 14, wherein the speculum is a retractor type and formed at least in part of wire.

22. The device of claim 1, wherein the evacuator body is a single uninterrupted loop of tubing having one occluded end, disposed proximally, substantially adjacent to a point at which the smoke exit portion is integral with and extends away from the evacuator body portion.

23. The device of claim 1, and further comprising fluid introduction structure connected to at least one of the evacuator body and the smoke exit portion, to thereby permit selective introduction of extraneous fluid to the surgical site.

24. The device of claim 23, and further wherein the fluid introduction structure includes a body having fluid exit structure and a portion connectable to a source of fluid connected to the body, the fluid introduction structure being connected to the evacuator body and smoke exit portion in overlying relationship thereto, and being functionally interchangeable therewith.

25. The device of claim 1, wherein the evacuator body and the smoke exit portion are formed of surgical grade tubing having an inside diameter in the range of about 0.5 mm to about 3.0 mm and an outside diameter in the range of about 2.0 mm to 4.0 mm.

26. The device of claim 1, wherein the device is formed at least in part of plastic.

27. The device of claim 1, wherein the device is formed at least in part of metal.

28. The device of claim 1, wherein at least a portion of the device is flexible.

29. The device of claim 1, wherein at least a portion of the device is rigid.

30. The device of claim 1, wherein the device is formed of materials suitable for presterilization and disposal after a single use.

31. The device of claim 1, wherein the device is formed of materials that are suitable for repeated resterilization and reuse.

32. The combination comprised of an eyelid speculum and a surgical laser smoke plume evacuator device, wherein the smoke plume evacuator device comprises an evacuator body which is formed to a shape which is suitable for placement in normal use position substantially entirely around and adjacent to an area of tissue upon which laser surgery is to be performed, the evacuator body defining a perimeter of the area of tissue and having structure for removing smoke therethrough, the structure for removing smoke therethrough lying in a plane adjacent to and distal to the area of tissue, wherein said structure comprises a longitudinal axis which is non-perpendicular to the tissue being treated a smoke exit portion in communication with the evacuator body, and extending away from the evacuator body, the smoke exit portion being connectable to a vacuum source, to thereby apply a vacuum to the evacuator body and cause smoke which is created during surgery by contact of the surgical laser with tissue to be removed from the area of tissue through the evacuator body and the smoke exit portion, and wherein at least one of the evacuator body and the smoke exit portion is connectable to the eyelid speculum.

33. The combination of claim 32, wherein the evacuator body of the smoke plume evacuator device is formed of tubing and the structure for removing smoke therethrough comprises at least one opening disposed on an internal aspect of the evacuator body and extending from a luminal surface of an internal aspect thereof to a nonluminal surface thereof and faces toward the area of tissue upon which surgery is to be performed, and further wherein the at least one opening is disposed less than 3.8 cm from a point of smoke producing surgical contact within the tissue area.

34. A method of removing a smoke plume created during surgery comprises:

selecting a smoke plume evacuator device having an evacuator body comprising two pieces of tubing each having a proximal end and a distal end in normal use position and, arranged adjacent to each other, but curving outwardly, away from each other and then inwardly, toward each other at proximally disposed free ends thereof to provide a perimeter substantially entirely around a surgical site, each of the free ends being occluded so that the application of a vacuum to the device will cause a vacuum to be pulled through the structure for removing smoke from the evacuator body, and each of the two pieces of tubing having a distally disposed end in normal use position, the distally disposed ends forming the smoke exit portion and being connectable to a vacuum source and the smoke exit portion being in communication with the evacuator body, positioning the evacuator body of the surgical smoke evacuation device around a surgical site so that the site is accessible via an inner aspect of the evacuator body, and so that at least some structure on the evacuator body inner aspect for removing smoke is disposed less than 3.8 cm from the smoke producing surgical treatment site, connecting the smoke exit portion of the evacuation device to a vacuum source, applying a vacuum to the smoke exit portion of the evacuation device, and initiating a smoke producing surgical procedure upon tissue at the surgical site, the smoke being produced exiting radially away from the surgical site via the structure for removing smoke on the evacuator body and then via the smoke exit portion toward the vacuum source.

35. The method of claim 34, wherein the smoke producing surgical procedure is a surgical laser treatment.

* * * * *